United States Patent [19]

Rossignol

[11] Patent Number: 5,578,621
[45] Date of Patent: Nov. 26, 1996

[54] BENZAMIDE DERIVATIVES

[76] Inventor: Jean-Francois Rossignol, 2650 Heron La. South, Clearwater, Fla. 34622

[21] Appl. No.: 301,407

[22] Filed: Sep. 8, 1994

[51] Int. Cl.$^6$ .................................................. A61K 31/425
[52] U.S. Cl. ................................... 514/371; 548/192
[58] Field of Search ............................. 548/192; 514/371

[56] References Cited

U.S. PATENT DOCUMENTS 3,950,351  4/1976  Rossignol ............................... 548/192

FOREIGN PATENT DOCUMENTS

| 716 | 8/1961 | France. |
|---|---|---|
| 1306603 | 9/1962 | France. |
| 2240010 | 3/1975 | France. |
| 2435905 | 4/1980 | France. |

OTHER PUBLICATIONS

R. Cavier et al., "Recherches sur les dérivés nitrés d'intérêt biologique", *European Journal of Medicinal Chemistry, Chimica, Therapeutica*, vol. 13 No. 6 1978 Paris Fr. pp. 539–543.

M. Dymicky et al., "Inhibition of Clostridium botulinum by 5–nitrothiazoles", *Antimicrobial Aents and Chemotherapy*, vol. 12, No. 3, Sep. 1977, pp. 353–356.

Dymicky, AntiMicrobial Agents and ChemoTherapy, 12(3) 353 (1977).

*Primary Examiner*—Robert Gerstl
*Attorney, Agent, or Firm*—Sughrue, Mion, Zinn, Macpeak & Seas

[57] ABSTRACT

The present invention relates to a new compound of formula I

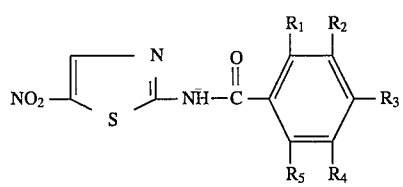

with one of the symbols $R_1$, $R_2$, $R_3$, $R_4$ and $R_5$ representing OH, whereas the remaining symbols represent H; to a pharmaceutical composition containing the said compound, and to the use of said compound as anti-parasital, anti-bacterial, anti-fungal agent.

The Prior Art

Nitrothiazole compound PH 5776 (2-(acetolyloxy)-N-(5-nitro 2-thiazolyl) benzamide) is a compound of formula II

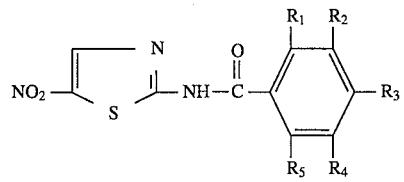

in which $R_1 = O$—$COCH3$ $R_2 = R_3 = R_4 = R_5 = H$ The preparation and uses of this compound are disclosed in U.S. Pat. No. 3,950,351, as well as in publication made by Applicant.

In U.S. Pat. No. 3,950,351, the compound of formula II is prepared by reacting

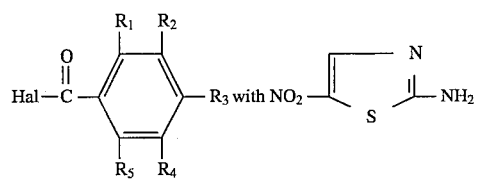

This reaction is not suitable for the preparation of pure compound of formula I

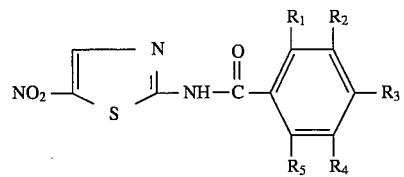

in which one of the symbols $R_1$, $R_2$, $R_3$, $R_4$ and $R_5$ represent OH, whereas the remaining symbols represent H.

Moreover, contrary to what could be expected from the prior art, i.e. that the presence of an acyloxy group was necessary for rendering the compound active and efficient against bacteria, parasites, . . . , it has now been found that the compound of formula I

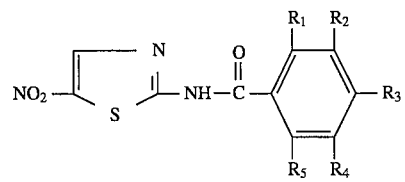

with one of the symbols $R_1$, $R_2$, $R_3$, $R_4$ and $R_5$ representing OH, whereas the remaining symbols represent H; had an excellent efficiency against parasites, bacteria, fungus although it does not contain an acyloxy group.

The compound of formula I had a substantially immediate action against parasite, fungus, bacteria.

7 Claims, 2 Drawing Sheets

BENZAMIDE DERIVATIVES

BRIEF DESCRIPTION OF THE INVENTION

The present invention relates to a new compound of formula i

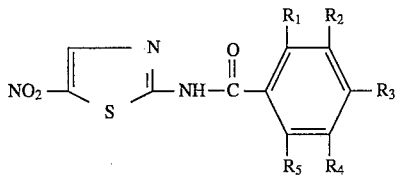

in which one of the symbols $R_1$, $R_2$, $R_3$, $R_4$ and $R_5$ represent OH, whereas the remaining symbols represent H.
Preferably, $R_1$=OH The invention relates also to a pharmaceutical composition comprising as active agent, a compound of formula I as described hereabove, preferably a compound of formula I in which $R_1$=OH.

According to an embodiment, the composition comprises, as active agent, a mixture of

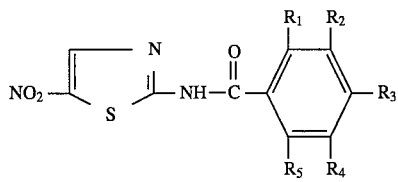

with $R_1$=OH and $R_2$=$R_3$=$R_4$=$R_5$=H and

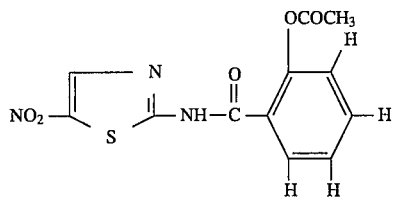

Such a composition combines a substantially immediate action against parasite, fungus, bacteria or a substantially immediate treatment of intestinal trouble and a some what retarded action or treatment.

Such a composition is thus suitable for treating human troubles or for preventing human troubles, such as parasitic infections, bacterial infections, fungal infections, diarrhea and other intestinal troubles.

In said composition, the weight content of formula III

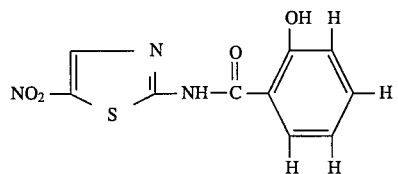

with respect to the weight of a mixture of compound of formula III

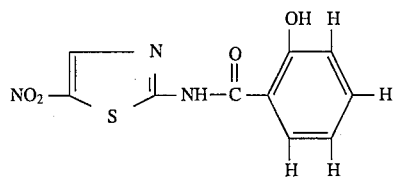

and compound of formula II

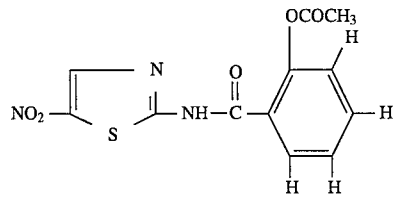

is comprised between 1 and 20%, preferably between 1 and 10%, more preferably between 1 and 5%.

The invention relates also to the use of a compound according to the invention, especially a composition according to the invention as anti-parasite agent, anti-bacterial agent, anti-fungal agent, . . . .

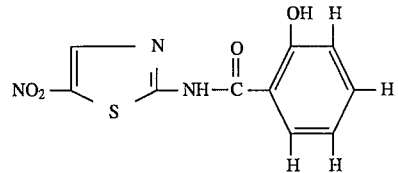

Figure 3:
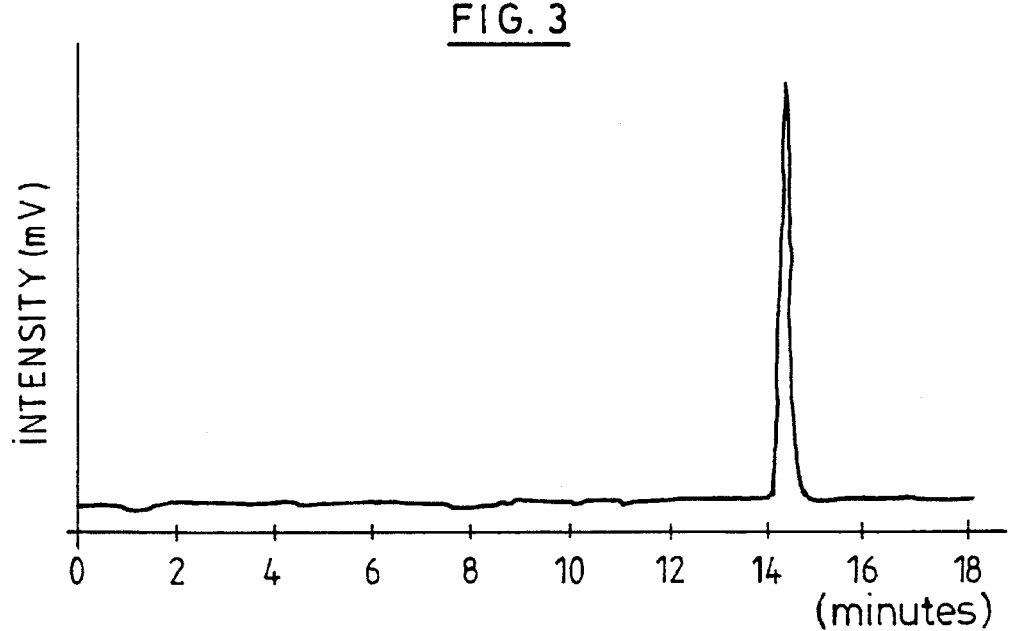
Figure 2:
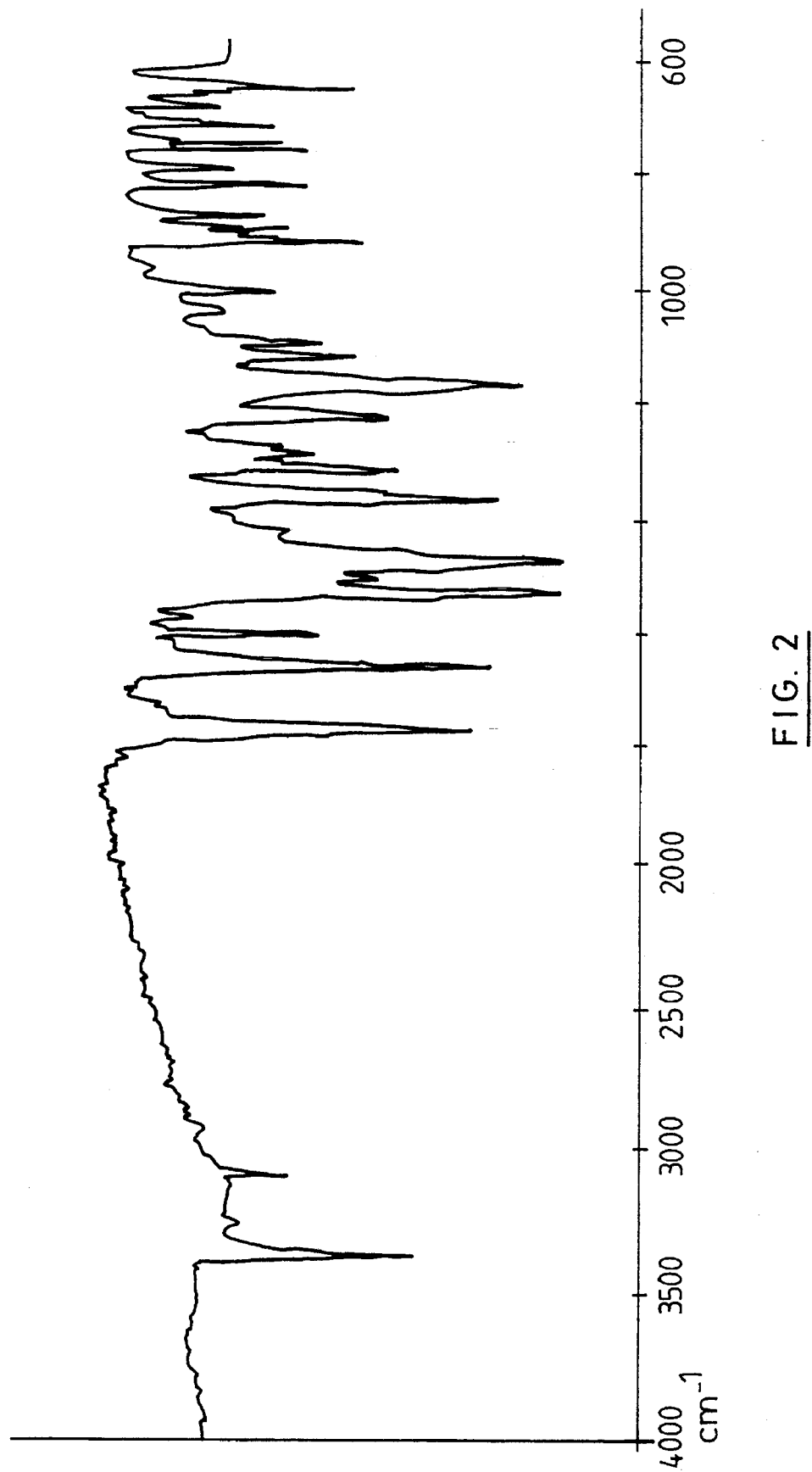

FIG. 2 is the IR spectrum of compound of formula III, and
FIG. 3 is the HPLC mass spectrum of compound of formula III.

DESCRIPTION OF THE INVENTION

The preparation of pure compound of formula I

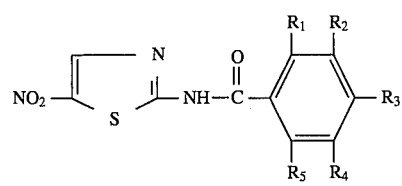

in which one of the symbols $R_1$, $R_2$, $R_3$, $R_4$ and $R_5$ represent OH, whereas the remaining symbols represent H, can be made from compounds of formula II

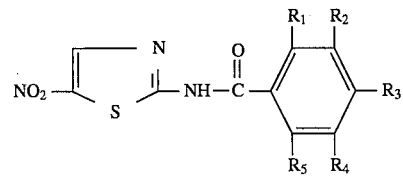

in which one of the symbols $R_1$, $R_2$, $R_3$, $R_4$ and $R_5$ is an acyloxy group, whereas the remaining symbols represent hydrogen.

The said compound is put in suspension in a weak mixture of hydrochloridric acid and water. The so treated compound is then filtered and washed with water. The washed compound is then possibly dried.

A specific example of preparation is given hereafter:
2 g of 2-(acetolyloxy)-N-(5-nitro 2-thiazolyl) benzamide (i.e. PH 5776) prepared according to the method disclosed in U.S. Pat. No. 3,950,351 is put in suspension in 20 ml of a 37% HCl solution. The medium was kept at 50° C. during 24° C. and was slowly stirred.

After said treatment, the medium was filtered so as to obtain solid particles. Said particles have then been washed with water until pH 7 and dried in an oven at 50° C.

The resulting product appears as yellow microcristalline needles, the melting point of which was 254° C. (melting point measured according to the capillary determination on a Mettler FP apparatus).

Figure 1:
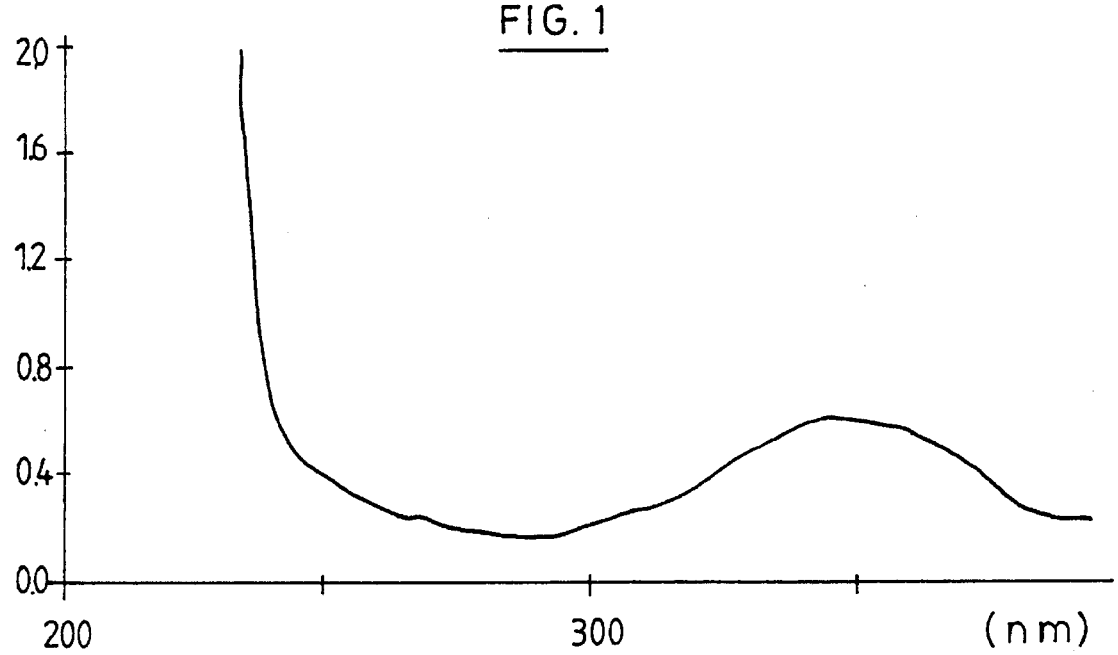
FIG. 1 is the UV spectrum of compound of formula III

The structure identification was carried out by centesimal analysis, UV spectrum (see FIG. 1), IR spectrum (see FIG. 2) and gas-chromatography-mass spectrum (see FIG. 3). The results of this identification are:

C10, H7, N3, O4, S1; 258 Calculated C 46,51% H 2,71% N 16,40% S 12,40% found 45,98% 2,63% 16,71% 12,67% $\lambda_{max}$=350 nm (OD=0.605).

A composition according to the invention has been prepared by mixing PH 5776 and the compound prepared hereabove, the weight content of said compound with respect to the weight of the said compound and PH 5776 being 4%.

During phase I, pharmacokinetics study was carried out on 6 volunteers who received a single 500 mg oral dose of the composition. Approximately 3 mcg/ml of 2-(hydroxy)-N-(5-nitro 2-thiazolyl) benzamide could be assayed in the blood by High Pressure Liquid Chromatography. This product was also excreted unchanged in urine during the first 24 hours following treatment. There is no trace of 2-(acetolyloxy)-N-(5-nitro 2-thiazolyl) benzamide in blood and urine.

During Phase II clinical studies conducted in a total of 80 patients, post-treatment repeated fecal examinations and/or vaginal smears revealed that 500 mg of the combination given twice a day for 3 to 7 consecutive days was highly effective (60–95%) against *Trichomonas vaginalis, Entamoeba histolytica, Gardia lamblia, Enterobius vermicularis, Ascaris lumbricoides, Necator americanus, Ancylostoma duodenale, Trichuris trichiura, Strongyloides stercoralis, Taenia saginata, Taenia solium, Diphylobottrium latum* and *Hymenolepis nana*. Tolerance was good and only a few epigastric pains, nausea, vomiting and diarrhea were observed in about 8–20% of patients depending on the duration of treatment. Blood chemistry and hematology carried out before and after treatment remained unafected by the composition.

In vitro studies against *Trichomonas vaginalis* has shown that while 2-(acetolyloxy)-N-(5-nitro 2-thiazolyl) benzamide had a Minimum Inhibitory Concentration of 0.5 to 1.25 mcg/ml, 2-(hydroxy)-N-(5-nitro 2-thiazolyl) benzamide in the same experimental conditions showed 1 to 1.25 mcg/ml. This is demonstrating that 2-(hydroxy)-N-(5-nitro 2-thiazolyl) benzamide has an antipara-sitic activity equivalent to that of 2-(acetolyloxy)-N-(5-nitro 2-thiazolyl) benzamide. However, these studies showed that 2(hydroxy)-N-(5-nitro 2-thiazolyl) had a substantially immediate action, which was not the case for 2-(acetolyloxy)-N-(5-nitro 2-thiazolyl) benzamide).

Finally in vitro studies has shown that the composition was effective against gram positive and gram negative aerobic bacteria such as *Staphylococcus aureus, Escherichia coli, Shigella sonei, Helicobacter pylori;* anaerobic bacteria such as *Bacteroides fragilis, Fusobacterium ulcerans, Veillonella alcadescens, Gardnerella vaginalis,* dermatophytes of yeasts fungi such as *Trichophyton mentographytes, Microsporum audovini, Epidermophyton nocosum* and *Candida albicans*.

By using a compound of formula I

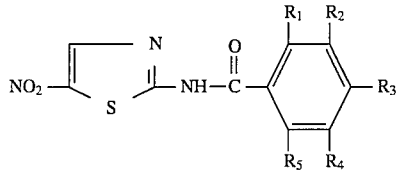

in which one of the symbols $R_1$, $R_2$, $R_4$ and $R_5$ represent OH, whereas the remaining symbols represent H, preferably a compound of formula III, even in very low amount, it was possible to increase the efficiency of compounds of formula II, especially of compound PH 5776.

What I claim is:

1. A pharmaceutical composition which comprises, as active agent, a mixture of the compound of formula (I):

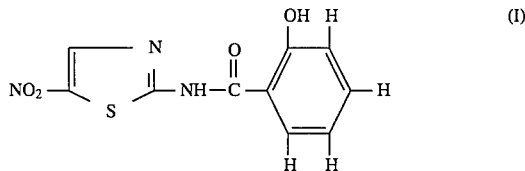

and a compound of formula (II):

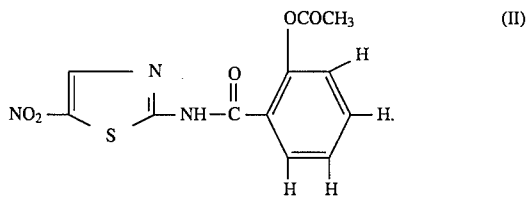

2. The pharmaceutical composition of claim 1, wherein the compound of the formula (I) is present in an amount of 1 to 20% by weight of the mixture.

3. The pharmaceutical composition of claim 1, wherein the compound of the formula (I) is present in an amount of 1 to 10% by weight of the mixture.

4. A method for treating parasite infections comprising administering to a host in need of treatment an effective amount of a mixture of a compound of formula (I):

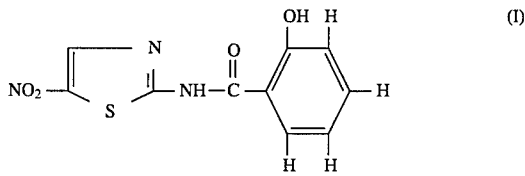

and a compound of formula (II):

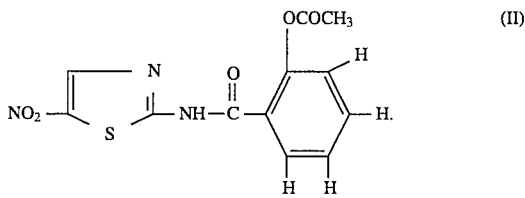

5. A method of treating bacterial infections comprising administering to a host in need of treatment an effective amount of a mixture of a compound of formula (I): and a compound of formula (II):

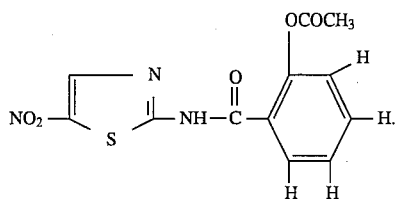

6. A method for treating fungal infections comprising administering to a host in need of treatment an effective amount of a mixture of a compound of formula (I):

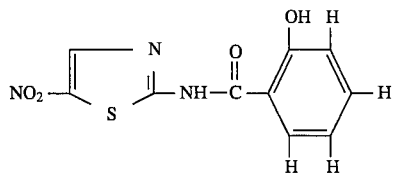

and a compound of formula (II):

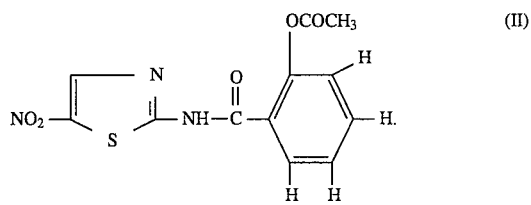

7. A method for increasing the efficacy of 2-(acetolyloxy)-N-(5-nitro 2-thiazolyl) benzamide comprising administering said 2-(acetolyloxy)-N-(5-nitro 2-thiazolyl) with an effective amount of a compound of formula (I):

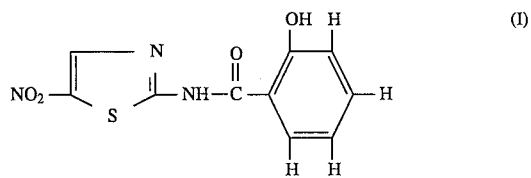

* * * * *

UNITED STATES PATENT AND TRADEMARK OFFICE
CERTIFICATE OF CORRECTION

PATENT NO.   : 5,578,621
DATED        : November 26, 1996
INVENTOR(S)  : Jean-Francois Rossignol It is certified that error appears in the above-identified patent and that said Letters Patent is hereby corrected as shown below:

On the title page, add item [73] Assignee:
--Romark Laboratories, L.C.
  Tampa, Florida 33607 --.

Signed and Sealed this

Sixteenth Day of December, 1997

Attest:

BRUCE LEHMAN

Attesting Officer

Commissioner of Patents and Trademarks